United States Patent

Buzby, Jr.

[11] Patent Number: 4,618,711
[45] Date of Patent: * Oct. 21, 1986

[54] ANTI-ARRHYTHMIC AGENTS

[75] Inventor: George C. Buzby, Jr., Blue Bell, Pa.

[73] Assignee: American Home Products Corporation, New York, N.Y.

[*] Notice: The portion of the term of this patent subsequent to Sep. 3, 2002 has been disclaimed.

[21] Appl. No.: 717,341

[22] Filed: Mar. 29, 1985

[51] Int. Cl.$^4$ ............... C07C 143/80; C07C 143/78; C07C 143/822

[52] U.S. Cl. .................................. 564/86; 564/91; 564/92

[58] Field of Search .................. 564/91, 92, 86; 260/46 SE; 558/390, 394

[56] References Cited

U.S. PATENT DOCUMENTS 2,233,296  2/1941  Nelles et al. ............... 564/92
4,034,112  7/1977  Smith ........................... 564/92

FOREIGN PATENT DOCUMENTS 37413  9/1972  Japan .......................... 564/86

OTHER PUBLICATIONS

Hediger et al, J.C.S. Chem. Comm., vol. 1, pp. 14–15 (1978).
Fleckenstein, Ann. Rev. Pharmacol., 17, 149–66 (1977).

Primary Examiner—Charles F. Warren
Assistant Examiner—R. A. Picard
Attorney, Agent, or Firm—Richard K. Jackson

[57] ABSTRACT

Compounds of the formula:

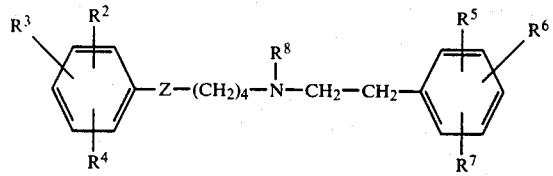

in which
Z is

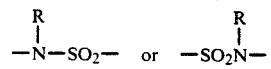

where R is hydrogen, alkyl, polyfluorinated alkyl, —CN, cyanoalkyl, cycloalkyl or cycloalkylalkyl;
$R^2$, $R^3$, $R^4$, $R^5$, $R^6$ and $R^7$, independently, are hydrogen, alkoxy, trifluoromethyl or halo;
$R^8$ is hydrogen or alkyl;

or a pharmaceutically acceptable salt thereof, are useful as anti-arrhythmic agents.

2 Claims, No Drawings

ANTI-ARRHYTHMIC AGENTS

BACKGROUND OF THE INVENTION

Pharmacological agents possessing the ability to block cellular transmembrane influx of calcium are capable of suppressing that portion of myocardial or vascular smooth muscle contractility which is dependent upon extracellular calcium. Church et al., Can. J. Physiol. Pharmacol., 58, 254 (1980); Fleckenstein, Calcium and the Heart, P. Harris and L. Opie, eds., Academic Press (1971); Nayler et al., Bas. Res. Cardiol., 76, 1 (1981); Calcium Blockers, S. Flaim and R. Zelis, eds., Urban and Schwartzenberg, (1982).

These pharmacological agents, termed calcium entry blockers, have been proven to be useful in the treatment of hypertension, cardiac arrhythmias, angina pectoris, and coronary artery vasospasm (a possible cause of sudden cardiac death syndrome). Circ. Res., 52, Suppl. I, (1983); Hypertension 5, Suppl. II, (1983). In theory, calcium entry blockers are thought to act by blocking calcium influx through discrete calcium channels (slow channels) in cell membranes. Various tissues exhibit relative differences in sensitivity toward the calcium blocking effect achieved by certain calcium antagonists, theoretically as a result of tissue specific differences in the calcium channels. Acta Pharmacol. Toxicol., 43, 5 (1978); loc. cit. 291 (1978); Microvascular Res., 5, 73 (1973); Am. Rev. Pharmacol. Toxicol., 17, 149 (1977). It is believed that the slow calcium current is responsible for activation of pacemaker cells in the sinoatrial node and the atrioventricular node of the heart. Verapamil, a known calcium channel blocking agent, is believed to slow conduction velocity through the atrio-ventricular node of the heart, in explanation of the mechanism of its anti-arrhythmic activity.

DESCRIPTION OF THE INVENTION

In accordance with this invention there is provided a group of compounds of the formula:

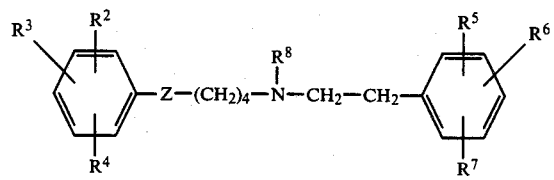

in which
Z is

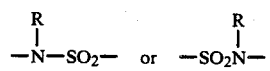

where R is hydrogen, alkyl of 1-6 carbon atoms, polyfluorinated alkyl of 1 to 6 carbon atoms, —CN, cyanoalkyl in which the alkyl moiety contains 1 to 3 carbon atoms, cycloalkyl of 3 to 6 carbon atoms or cycloalkylalkyl of 4 to 8 carbon atoms;

$R^2$, $R^3$, $R^4$, $R^5$, $R^6$ and $R^7$, independently, are hydrogen, alkoxy of 1-3 carbon atoms, trifluoromethyl, —Cl, —Br or —F;

$R^8$ is hydrogen or alkyl of 1 to 6 carbon atoms;
or a pharmaceutically acceptable salt thereof.

The compounds of this invention represent analogues of the compounds disclosed and claimed in my co-pending application Ser. No. 609,151, filed May 11, 1984, now U.S. Pat. No. 4,539,426, issued Sept. 3, 1985, which have surprisingly been found to be as potent as the most potent compound of my copending application.

The pharmaceutically acceptable salts of the anti-arrhythmic agents of this invention are prepared directly by neutralization of the free base or by metathetical displacement. The physiologically acceptable salts may be formed with organic or inorganic acids such as hydrochloric, hydrobromic, phosphoric, sulfuric, sulfonic, nitric, methylsulfonic, acetic, maleic, succinic, fumaric, tartaric, citric, salicylic, lactic, naphthalenesulfonic acid, and the like.

The compounds of this invention are prepared by several stage processes involving alkylation reactions performed on amines or sulfonamides or both. Briefly, an appropriately substituted aromatic amine

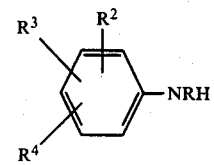

in which $R^2$, $R^3$, $R^4$ and R are as defined above, is reacted with $ClSO_2$-$(CH_2)_4$-Cl, and the product is employed to alkylate an aralkylamine of the formula

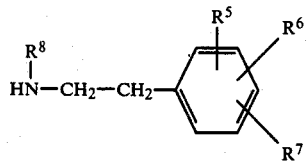

where $R^{5-8}$ are as defined, supra. This reaction sequence affords the N-aromatic-propanesulfonamide type compounds of this series. The benzenesulfonamide type compounds of this series are produced in analogous manner by reaction of an appropriately substituted aromatic sulfonamide

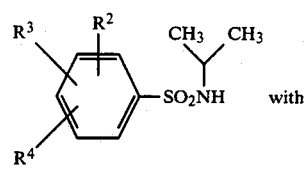

with

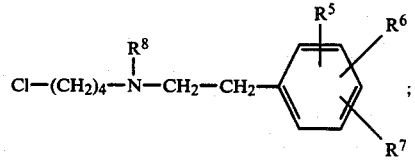

or by reaction of an aromatic sulfonyl halide with an omegahydroxy alkylamine followed by N-alkylation and replacement of the hydroxyl group with a halogen, and alkylation of the appropriate aralkylamine. Similarly, the hydroxyl group may be oxidized to an aldehyde which may be reacted with an appropriately substituted aralkylamine by reductive amination. The intermediates employed are either known compounds or are prepared from literature compounds by procedures well within the skill of the medicinal chemist.

The compounds of this invention exhibit $Ca^{+2}$ antagonism in rabbit aortic smooth muscle when tested by a modified procedure from that described by Brockaert et al., Eur. J. Pharmacol., 53, 281 (1979). Here, transverse strips (10 mm×2.5 mm) from the thoracic aorta were cut and suspended vertically in a jacketed (37° C.-50 ml volume) organ bath in physiological saline solution (PSS) aerated with 95% $O_2$/5% $CO_2$. The composition of PSS was as follows (mM): NaCl 112, KCl 5, $NaHCO_3$ 25, $KH_2PO_4$ 1, $MgSO_4$ 1.2, $CaCl_2$ 2.5, dextrose 10. The lower end of each tissue strip was attached to a fixed post and the upper end to a Statham UC-4 transducer. Changes in force development were recorded on a Beckman Dynograph Polygraphic Recorder.

Following equilibration, the muscles were contracted in a depolarizing solution of PSS in which 100 mM KCl was substituted for an equimolar concentration of NaCl. Following attainment of steady-state isometric force (20 min.), the test compound was added to afford a final concentration of $1 \times 10^{-5}M$. The inhibitory effect, expressed as percent relaxation, was determined from the mean of two experiments twenty minutes after the addition of the compound being tested.

In addition, the compounds of this invention demonstrate an inhibitory influence on arterial $Ca^{+2}$-calmodulin dependent myosin light chain phosphorylation and subsequent contractile protein function when tested in standard experimental procedures for these inhibitory properties.

As such, the compounds of the invention present an activity profile consistent with that of anti-arrhythmic agents, which utility was proven by in vivo experiments in the standard experimental animal as follows:

Rats weighing between 400-500 gms were anesthetized with 35-40 mg/kg Na pentobarbital i.p. Rats were close-clipped on the neck and left side prior to cannulation of the jugular vein and tracheotomy. In some experiments, a catheter was introduced into the carotid artery for measurement of arterial blood pressure. Respiration was provided by a Harvard Model 681 respirator at a rate of approximately 55/min and a volume of 4 cc per cycle. The rat was then placed upon its right side and the heart was exposed by making an incision and separating the ribs. 4-0 silk on taper RB-1 needle was passed under the left anterior descending coronary artery (LAD) at a location just under the tip of the left atrial appendage. The suture was left to be tied upon occlusion. Lead II ECG and cardiotachometer output were recorded on a Beckman R612.

The rat was allowed to stabilize for several minutes before the administration (1 mg/kg) of drug via the cannulated jugular vein. Compounds were suspended in carbowax, with total dose volumes kept below 0.20-0.25 ml. Fifteen minutes after dosing, the LAD was occluded by tying the suture. This procedure provokes severe ventricular arrhythmias, terminating in ventricular fibrillation and death in approximately 73 percent of animals given vehicle only. Data were analyzed based on statistical analysis of heart rate fluctuations. Output from a Beckman cardiotachometer was digitized at 200 msec/pt using a Nicolet 3091 digital oscilloscope, and the data analyzed to yield mean±variance of the rate for each 1 minute period (300 points). The measured variance for the period 5-11 minutes post-occlusion was well correlated with the severity of the observed ventricular arrhythmias, and provided a quantitative measure for the relative antiarrhythmic effectiveness of the compound being tested.

For the purpose of these coronary ligation (C.L.) experiments, the actual mortality rate, expressed as a percentage of the animals employed, was obtained for purpose of comparison with the mortality rate of 73 percent in vehicle-treated animals.

Thus, these data establish the compounds of this invention as $Ca^{+2}$ antagonists which are useful as anti-arrhythmic agents functioning more at the vascular level than other known $Ca^{+2}$ entry blockers. It has been observed that compounds of this invention inhibit arterial $Ca^{+2}$-calmodulin dependent myosin light chain phosphorylation and subsequent contractile protein function.

Based upon the activity profile elicited by the compounds of this invention in the above-described standard scientifically recognized test models, the compounds are established as anti-arrhythmic agents useful in the treatment of cardiac arrhythmias and conditions characterized by coronary arteries vasospasm. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established at from 1 to about 50 milligrams per kilogram host body weight to be administered in single or plural doses as needed to relieve the arrhythmatic dysfunction. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 25 milligrams to about 4 grams) of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following example illustrates the preparation of a representative compound of this invention. After the example, the $Ca^{+2}$ antagonist activity of the compound is presented in terms of percent relaxation (P.R.) at $10^{-5}M$ concentration unless indicated otherwise. Similarly, the percentage mortality of standard experimental test animals upon coronary ligation (C.L.) is presented for comparison with the control mortality rate of 73 percent of animals receiving vehicle alone.

EXAMPLE 1

3,4-Dichloro-N-[4-[[2-(3,4-dimethoxyphenyl)ethyl]methylamino]butyl]-N-(1-methylethyl)benzenesulfonamide 3,4-Dichlorobenzene sulfonyl chloride (98.3 g, 0.4 m) in methylene chloride (200 ml) was added dropwise to 4-amino-1-butanol (35.69 g, 0.4 m) and diisopropyl ethylamine (51.75 g, 0.4 m) in methylene chloride (500 ml). After workup the crude product, N-(4-hydroxybutyl)-3,4-dichlorobenzenesulfonamide, was obtained as a gummy white crystalline solid, m.p. 78°-80° C., identified by combustion and spectral data.

The product of the preceding paragraph (40.10 g, 0.134 m) in dry dimethylformamide (400 ml) was treated with NaH/mineral oil 60% (5.38 g, 0.134 m) and the reaction stirred one hour at room temperature. Then 2-bromopropane (16.5 g, 0.134 m) was added and the reaction heated at a temperature of 35° to 50° C. over the weekend. The reaction was worked up and the crude product chromatographed on dry column alumina (1 kg) with 1:1 ethyl acetate/hexane to provide the N-isopropylated product (16.09 g) as a light yellow oil.

Pyridine-chromic acid complex was prepared by adding chromium trioxide (26.4 g, 94 m. moles) to pyridine (41.76 g) in methylene chloride (660 ml). The reaction mixture was stirred at room temperature for ¾ hours. Then N-isopropyl-N-(4-hydroxybutyl)-3,4-dichlorobenzenesulfonamide prepared in the preceding paragraph (15.01 g) in methylene chloride (150 ml) was added all at once. After ½ hour the liquid was decanted and washed with 5% aqueous NaOH, 5% aqueous HCl, 5% aqueous NaHCO3 and finally brine. After removal of solvent there was obtained N-isopropyl-N-(4-oxobutyl)-3,4-dichlorobenzenesulfonamide as a dark oil (9.01 g) which started to nicely crystallize but was used below without further purification.

The aldehyde prepared in the preceding paragraph (8.90 g, 0.027 m) and N-methyl-homoveratrylamine (5.29 g, 0.027 m) in absolute ethanol (100 ml) containing PtO2 (0.6 g) was shaken under hydrogen (7 hours) and the reaction filtered and stripped to provide the crude product (13.32 g) as a dark greenish gum. This material was chromatographed, after removal of a small amount of insoluble solid, on dry column silica gel (500 g) with 30% methanol/70% ethyl acetate to provide the title compound (7.26 g) as a clear white gum.

Analysis for: $C_{24}H_{34}N_2Cl_2O_4S$: Calculated: C, 55.70; H, 6.62; N, 5.41. Found: C, 55.63; H, 6.59; N, 5.29.

P.R.=68%.
C.I.=0%.

What is claimed is:

1. A compound of the formula:

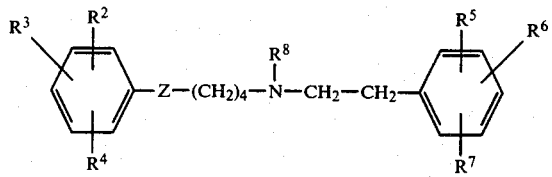

in which
Z is

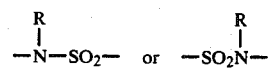

where R is hydrogen, alkyl of 1-6 carbon atoms, polyfluorinated alkyl of 1 to 6 carbon atoms, —CN, cyanoalkyl in which the alkyl moiety contains 1 to 3 carbon atoms, cycloalkyl of 3 to 6 carbon atoms or cycloalkylalkyl of 4 to 8 carbon atoms;

$R^2$, $R^3$, $R^4$, $R^5$, $R^6$ and $R^7$, independently, are hydrogen, alkoxy of 1-3 carbon atoms, trifluoromethyl, —Cl, —Br or —F;

$R^8$ is hydrogen or alkyl of 1 to 6 carbon atoms; or a pharmaceutically acceptable salt thereof.

2. A compound of claim 1 which is 3,4-dichloro-N-[4-[[2-(3,4-dimethoxyphenyl)ethyl]methylamino]butyl]-N-(1-methylethyl)benzenesulfonamide or a pharmceutically acceptable salt thereof.

* * * * *